United States Patent [19]

Costa et al.

[11] Patent Number: 4,665,898
[45] Date of Patent: May 19, 1987

[54] MALIGNANCY TREATMENT

[75] Inventors: Jonathan L. Costa, Bethesda, Md.; Gunter A. Hofmann, San Diego, Calif.

[73] Assignee: Maxwell Laboratories, Inc., San Diego, Calif.

[21] Appl. No.: 613,507

[22] Filed: May 23, 1984

[51] Int. Cl.$^4$ .............................. A61B 17/52
[52] U.S. Cl. ...................................... 128/1.3
[58] Field of Search ................... 128/1.3–1.5, 128/804; 422/22; 426/234, 237, 238, 241

[56] References Cited

U.S. PATENT DOCUMENTS

| | | | |
|---|---|---|---|
| 3,368,155 | 2/1968 | Priore | 128/1.3 |
| 3,467,076 | 9/1969 | Frisch et al. | 128/1.3 |
| 4,134,395 | 1/1979 | Davis | 128/1.3 |
| 4,323,056 | 4/1982 | Borrelli et al. | 128/1.3 |
| 4,510,925 | 4/1985 | Constantinescu | 128/1.3 |
| 4,524,079 | 6/1985 | Hofmann | 426/234 |

FOREIGN PATENT DOCUMENTS

| | | | |
|---|---|---|---|
| 0040053 | 11/1981 | European Pat. Off. | 128/1.3 |
| 0039988 | 11/1981 | European Pat. Off. | 128/1.3 |
| 2253686 | 11/1974 | Fed. Rep. of Germany . | |
| 2370483 | 7/1978 | France | 128/1.3 |
| 1416335 | 12/1975 | United Kingdom | 128/1.3 |

Primary Examiner—Edward M. Coven
Assistant Examiner—Max F. Hindenburg
Attorney, Agent, or Firm—Fitch, Even, Tabin & Flannery

[57] ABSTRACT

A body part of an animal afflicted with malignant cells is disposed within a magnetic coil and subjected to a plurality of magnetic field pulses, the pulses having intensities of between about 1 and about 100 Tesla and characteristic frequencies of between about 5 and about 1000 kHz. The pulsed magnetic field selectively inactivates and/or destroys malignant cells with relatively little damage to normal tissue as compared to conventional radiation therapy procedures.

15 Claims, 1 Drawing Figure

U.S. Patent  May 19, 1987  4,665,898
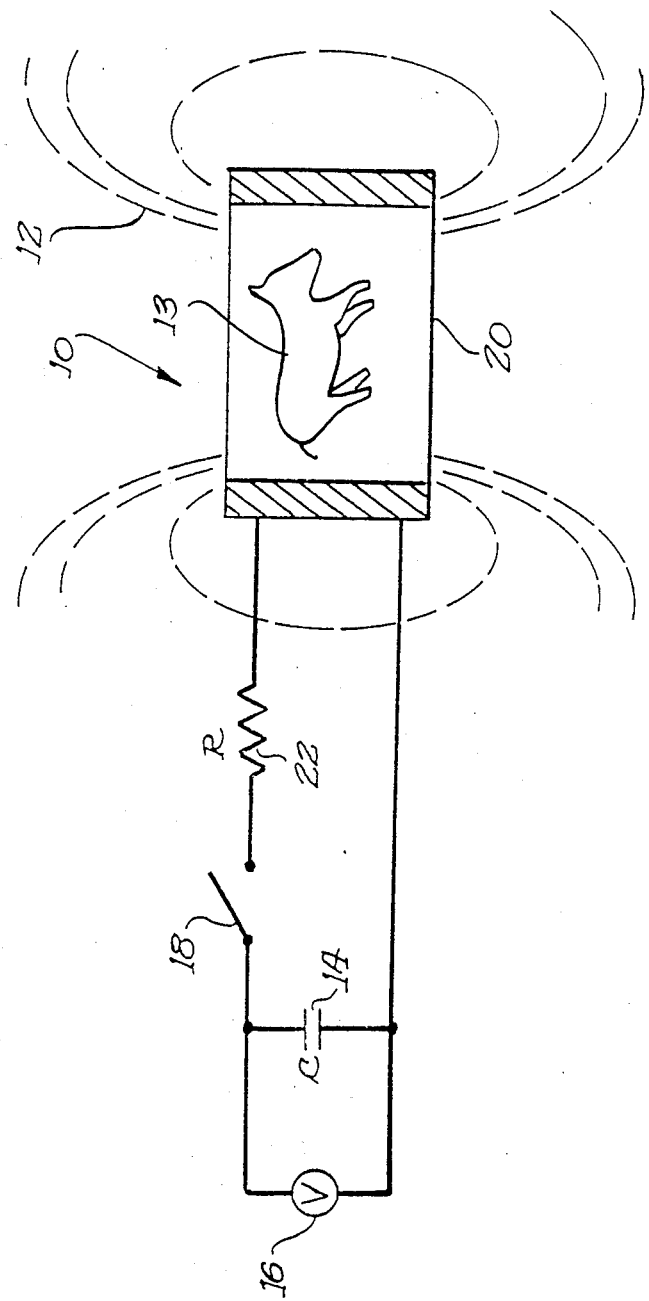

MALIGNANCY TREATMENT

The present invention relates to a method or treating cancer and more particularly to destroying malignant cells with a pulsed magnetic field.

The terms "malignancy" and "cancer" generally refer to an uncontrolled growth of abnormal cells. To successfully treat cancer, the abnormal cells must be eliminated or their growth must be arrested or significantly retarded. In some cases, particularly where the malignancy is localized and accessible, the cancer is successfully treated by surgical removal of the cancerous tumor. In other cases, particularly where the tumor is inaccessible or where the malignancy has metastasized, e.g., systemically, treatment often involves procedures, such as chemotherapy or ionizing radiation therapy, which kill malignant cells and/or retard their growth. Invariably, substantial damage to normal tissues is attendant on such methods, and a critical factor in all applications of such methods is the relative kill ratio of the clonogenic malignant cells to normal cells.

X-ray radiation is one of many procedures used in the therapeutic treatment of cancers. In general, the applied radiation is sufficient to destroy the reproductive integrity of a tumor cell. In such a procedure, it is necessary to kill every clonogenic malignant cell or the cancer will regrow. In general, not all cells in a malignancy are clonogenic, and a residual population fraction of $10^{-2}$ to $10^{-3}$ may be small enough for the malignancy not to recur. The application of ionizing radiation has certain contraindictions, such as the destruction of normal cells and in some cases the suppression of the immune system.

The kill mechanisms for exposure to ionizing radiation follow a hierarchial pattern. At very high doses in the range of 10,000 rad, the cells are killed through the deactivation of enzymes. In the range of 1,000 rad, cells may be killed through the rupture of their outer membranes. In the lower dose range of about 100 rad, the cells continue to function but suffer damage to chromosomes or other reproductive components and do not continue to subdivide and reproduce normally. At very low doses in the range of 10 rad, ionizing radiation may delay cell division but will not destroy the population. One of the critical areas which must be evaluated relates to the effect of a procedure intended to selectively kill malignant cells on hematopoietic, gastro-intestinal and central nervous system functions. In the case of ionizing radiation, limitations associated with continued function of the bone marrow, small intestine, and brain, at threshold levels above 100, 500, and 2,000 rad respectively, limit the duration and intensity of ionizing radiation therapy.

SUMMARY OF THE INVENTION

Herein, it is discovered that high intensity magnetic fields, applied in short pulses with moderate frequencies, can be used to selectively destroy or otherwise inactivate malignant cells within tissue of a living animal. Selective inactivation of malignant cells within animal tissue subjected to a pulsed magnetic field is accomplished without noticeable deterioration of gross characteristics of normal tissue. Substantially no heat is generated in the tissues, even in tissue which is sequentially subjected to a high number of pulses.

BRIEF DESCRIPTION OF THE DRAWING

The FIGURE is a diagrammatic illustration of a rat being treated within an electromagnetic coil and a simplified circuit associated with the coil for generating a pulsed magnetic field within the coil.

DETAILED DESCRIPTION OF A PREFERRED EMBODIMENT

In accordance with the present invention, animals or animal body parts are subjected to high intensity, moderate frequency magnetic field pulses to selectively kill or inactivate malignant cells within the tissues. The whole or portions of an animal body (the term "animal" is used herein to include humans, although initial experiments have been carried out on lower animals) can be subjected to the pulsed magnetic field. This process is carried out with a minimum effect on normal cells and without altering the gross characteristics of the subjected normal tissues.

It is found that subjecting body parts containing cancerous tissue to a plurality of magnetic field pulses, with characteristic frequencies above about 5 kHz and intensities above about 1 Tesla, will either arrest the growth of tumors or progressively reduce the number of cancerous cells, resulting in remission of tumors. Tissue treated with pulsed magnetic fields according to the present invention are not significantly heated, and thus there is no thermal discomfort to the subject and no burning of tissue whatsoever. Unlike X-ray or other ionizing radiation techniques, inactivation of cells is not achieved by an ionization mechanism, and there is no apparent alteration of the gross and functional characteristics of normal tissue.

Illustrated diagrammatically in the FIGURE is an electromagnetic coil 10 and associated circuitry which produce magnetic pulses of moderate frequency and high intensity. Apparatus of the general type illustrated is currently used for metal forming. An example of suitable apparatus is that sold under the trademark Magneform by Maxwell Laboratories, Inc. A cylindrical metallic object placed within the coil and exposed to intense magnetic pulses, represented by flux lines 12, is subjected to strong radial stresses which radially deform the object. The surprising discovery was made that by placing rats 13, which are inflicted with induced cancer tumors, within the magnetic coil and subjecting the rats to high intensity pulsed fields at moderate frequencies, arrest of tumor growth and/or pronounced remission of the tumors resulted.

The magnetic field in the coil is produced upon discharge of a bank of capacitors 14. The capacitor bank is charged from a source 16, and when a switch 18 is closed, completing the circuit that includes the capacitor bank and the coil, an oscillating or unipolar current can be generated between the plates of the capacitors. The oscillating current, in turn, generates a pulsed magnetic field which is concentrated within the region 20 bounded by the coil. The characteristic frequency of the pulsed field is determined by the capacitance of the capacitors and the resistance and inductance of the circuit, which are primarily determined by a resistor 22 and the inductance of the coil 10. Immediately subsequent to closing the switch, an intense magnetic field is produced by current flowing in one direction. As the current changes direction, the magnetic field changes polarity. In one particular circuit, the oscillating current, and hence, the oscillating magnetic field, rapidly decreases after about ten oscillations, dropping to a few percent of the original magnetic field strength. Herein, magnetic field intensities refer to the intensities of the initial peaks.

The effect of the pulsed magnetic field on animal tissue is far different than the effect of the pulsed magnetic field on metallic objects. Biological materials have very substantially reduced electrical conductivity (or very substantially increased electrical resistivity) relative to metals and are not similarly deformed. Furthermore, the high electrical resistivity (generally above 25 ohms-cm and almost invariably above 10 ohms-cm) of biological materials assures that the interior regions of the material are not excessively shielded from the coil-generated magnatic field by induced eddy currents.

The method is applicable to practically any type of tissue and is believed applicable for treatment of most types of malignancies.

The intensity of the magnetic field that is used may be as low as about 1 Tesla and about as high as about 100 Tesla, and preferably the field intensity is between about 1 and about 50 Tesla. The actual intensity of the magnetic field used depends on the type of tumor being treated and the location of the tumor within the body.

Tumor destruction is most effective when pulsed fields are used having characteristic frequencies in the range of from about 5 to about 1000 kHz. This frequency range is described herein as a moderate frequency range. In comparison, microwave frequencies are several orders of magnitude higher, i.e., in the megaherzt/gigahertz range. Frequencies above 1000 kHz tend to heat tissue.

Total typical exposure time of a living animal to the magnetic field is minimal, ranging from about 100 microseconds up to about 1 second in each therapy session. With reference to the above-described apparatus, exposure time can be considered the number of pulses multiplied by the duration of each pulse. Herein, pulse duration is considered to be the period extending from initiation to the poirt that the substantially decayed field has a negligible effect. In each session, an animal is exposed to at least 1 and up to 1000 magnetic pulses. Generally a living animal would be subjected to at least ten puses at each. therapy session and up to one hundred pulses. An animal will be subjected to additional sessions until tumor remission is achieved.

At the frequencies and intensities of the pulses, heating of body tissues is of minimal significance, and a practically unlimited number of pulses can be administered without detectable heating of body tissues.

The reason that tumor cells are killed or rendered reproductively inactive has not yet been determined, and applicants are not bound by any particular theory. However, it is suggested that in the case of a pulsed magnetic field energy might be coupled into magneto-active parts of critical large molecules. Within the intensity range of 1–50 Tesla, the amount of energy per pulse coupled to one dipole is $10^{-4}$ to $10^{-2}$ eV. With several pulses and a collective assembly of dipoles, enough local actlvation may result in destruction of a covalent bond, which typically has an energy in the vicinity of about 1 eV.

Breakage of certain bonds in critical large molecules, particularly in the genetic material, is likely to either kill the cell or renier the cell incapable of reproducing itself. Mallgnant cells are more susceptible to destruction and/or inactivation by a pulsed intense electromagnetic field because the field may create eddy currents that are unique to the tumor. These localized eddy currents may cause effects that are deleterious to the viability and/or reproductive capability of the tumor cells. Alternatively, there may be macromolecules unique to malignant cells which are especially magnetically susceptible. However, the invention is not considered to be limited to any particular theory of why the method of treatment is effective. Another possible alternative is that the pulsed magnetic field interferes with the transfer of free radicals or electrons through a chain of macromolecules that are unique to malignant cells.

If the reproducing tumor cells can be reduced below a threshold population, normal anti-tumor mechanisms in the body may be sufficient to counter a residual population of clonogenic tumor cells. After the tumor is eliminated, natural regenerative processes may be relied on to repair or mitigate any damage to normal tissue.

It is understood that the extent of treatment is a trade-off between some damage to normal tissue versus the benefits derived from tumor abatement or elimination. However, experimental results to date (see Example 2 below) indicate that the method of the invention is far less damaging to normal tissue than is ionizing radiation. The relatively little damage to normal tissue as compared to that induced by treatment with ionizing radiation decreases the time required for repair or regeneration of normal tissues.

Furthermore, treatment with a pulsed magnetic field does far less damage to the natural immune system than does radiation treatment or chemotherapy. Frequently, a patient who is treated extensively with ionizing radiation and/or with chemotherapy will experience an almost complete breakdown of the immune system. Subsequent to treatment, the immune system may take up to a year to recover, particularly with respect to immunity to viral infections. As a result, even if a patient is cured of the malignancy by radiation and/or chemotherapy, he is subject to debilitating disease or even death by infections to which his body would ordinarily have built up immunity. with the magnetic treatment described herein, there has been no evidence of major immune system break-down.

A secondary advantage of the procedure of the present invention relative to radiation procedures is that it poses no hazard to the technician performing the process. The high intensity magnetic field exists only within the coil and immediately therearound. Within a very short distance from the coil, the magnetic field drops off dramatically. For example, whereas the field generated by a coil may have an intersity of 5 Tesla in the interior of the coil, within abort 2 meters exterior to the coil, the intensity drops off to below $10^{-4}$ Tesla, a value comparable to the magretic field of the earth. Thus, providing that the teclnician is positioned a reasonable distance from the activated coil, there is substantially no likelihood of cells in the tissues of the technician being affected in a manner similar to the cells of the animal within the coil, and the process may be operated without any special shielding. Of course, the approximate distances increase in proportion to coil dimensions. One exception to this is that, as is the case with microwave apparatus, it should not be operated in the presence of persons wearing certain electrical or electronic prosthetic devices, such as pacemakers.

The invention will now be described in greater detail by way of specific examples.

EXAMPLE 1

In this experiment, the destructive effects of a high intensity, moderate frequency, pulsed magnetic field were compared for different types of cells grown in vitro, including both normal cells and malignant cells.

The effect of the pulsed magnetic field was examined on five types of cell lines: normal monkey kidney, normal mouse fibroblast, normal epithelial, undifferentiated carcinoma, and embryonal carcinoma. Cells were grown in confluent monolayers on Petri dishes and were treated briefly with trypsin. Supernatant liquid containing free-floating cells was removed, and test tubes containing aliquots of the free-floating cells were held at room temperature for the duration of the experiment. Tubes of cells were placed into the 4-inch coil of a conventional Magneform machine (Maxwell Laboratories) and given 8 pulses with the machine set to deliver approximately 10 kilojoules of energy at an intensity of 5 Tesla and a frequency of 8 kHz. As a control, tubes of cells were handled similarly but were not exposed to the magnetic field. Trypan blue was added to the test tubes to a final concentration of 0.2%. Aliquots of the cells were counted utilizing a hemocytometer and a light microscope; the total number of cells present per ml and the percentage staining with trypan blue, representing the percentage of killed cells, were calculated. Cells were ennumerated approximately 2 and 18 hours after treatment.

A summary of the results is presented in Table 1 below.

TABLE 1
EFFECTS OF BRIEF EXPOSURE TO A RAPIDLY VARYING MAGNETIC FIELD ON VARIOUS TYPES OF CELLS IN VITRO

| CELL TYPE | CELLS COUNTS PER ML | | PERCENT OF CELLS STAINED WITH TRYPAN BLUE | | |
|---|---|---|---|---|---|
| | Cells Counted Before Exposure | Cells Counted 18 hours After Exposure | Nonexposed Cells Observed After 18 Hours | Exposed Cells Observed After 2 h. | Exposed Cells Observed After 18 h. |
| Normal epithelial cells | $40 \times 10^4$ | $31 \times 10^4$ | 10% | 8% | 14% |
| Normal mouse fibroblasts | $5 \times 10^4$ | $7 \times 10^4$ | 11% | 7% | 2% |
| Normal monkey fibroblasts | $123 \times 10^4$ | $115 \times 10^4$ | 1% | 2% | 17% |
| Undifferentiated carcinoma | $30 \times 10^4$ | $35 \times 10^4$ | 1% | 3% | 32% |
| Embryonal carcinoma | $270 \times 10^4$ | $330 \times 10^4$ | 8% | 15% | 29% |

As can be seen from Table 1, the number of dead cells eighteen hours after exposure was significantly higher in the two malignant cell lines, e.g., by a factor of about two or more compared to normal cells.

EXAMPLE 2

In this experiment, albino rats with induced or transplanted tumors were subjected to high intensity, moderate frequency pulsed fields, and the effect of this field on the tumors was examined.

The following five groups of female albino rats were prepared: (1) 6 Sprague-Dawley rats bearing no tumors, (2) 7 Sprague-Dawley rats given a single oral feeding of dimethyl-benzanthracene (DMBA) approximately 1 month previously, inducing primary mammary carcinomas in each, (3) 6 Buffalo rats given 3 successive intravenous doses of N-nitrosomethyl urea (NMU) approximately 3 weeks previously, inducing primary mammary carcinomas in each, (4) 6 Buffalo rats, each with an NMU-induced mammary carcinoma transplanted to the popliteal region, (5) 6 Fisher rats, each with a mammary carcinoma of the 13762E/F344 line, transplanted to the popliteal region. If left untreated, all of the types of tumors would generally grow to a size of 20–30 cm$^3$, at which time the tumors would ulcerate. Rats having ulcerated tumors would generally die of secondary causes, such as infection, and in laboratories, rats are generally sacrificed at time of tumor ulceration for humane reasons. The mammary carcinomas in rats bearing primary tumors (groups 2 and 3) were measured in size (length and width measurements with a pair of calipers) for a period of 8 days prior to the start of the experiment. Tumors in rats bearing transplanted tumors were measured for a period of 3 days prior to the experiment. All groups of rats were given food and water ad libitum during the period of examination.

The rats were exposed once daily to a series of intense magnetic field pulses of brief duration. Two instruments were used, a conventional Magneform machine with a 4-inch diameter coil capable of storing 8 kilojoules of energy, and a high frequency Magneform machine with a 1-inch diameter coil capable of storing 9.6 kilojoules of energy. With the conventional Magneform machine, the entire rat was placed inside the coil volume and subjected to a series of twenty 5 Tesla, 8 KHz pulses. With the high frequenry Magneform machine, tumor-bearing areas were either placed inside the coil, or apposed as closely as possible to the top of the coil, and were subjected to five 18 Tesla (at the center of the coil), 250 kHz pulses. For the first 3 days of the experimental period, each rat was anesthetized with sodium pentobarbital (given by intraperitoneal injection) prior to exposure to the magnetic field. After this time, un-anesthetized rats to be irradiated in the conventional Magneform machine were placed in a cloth enclosure which fit inside the coil volume. Rats to be irradiated in the high frequency Magneform machine were anesthetized. During the experimental period, each tumor was measured with calipers daily prior to exposure to the magnetic field.

The high frequency Magneform machine was employed for 1 rat in group 1, 2 rats in group 2, 2 rats in group 3, 2 rats in group 4, and 2 rats in group 5; all the other rats were treated with the conventional Magneform machine. In group 4, two rats died of an apparent overdose of anesthesia (respiratory arrest) prior to exposure for the third time.

At the conclusion of the treatment of 6 days, the rats were observed for an additional period of time, generally about 16 days, during which tumor sizes were measured daily or every other day until the animals were sacrificed.

All of the rats of the control group 1 remained healthy throughout the experiment, exhibiting no adverse reaction to exposure to the magnetic field.

A summary of tumor data of rat groups 2-5 is presented in Table 2 below.

The remaining two rats were treated in an identical manner but at ¼th the field intensity, i.e., 1.2 Tesla, 8KHz, 20 pulses. One of these died on day 58 while the tumor size of the other had decreased in size from 1.6 cm³ on day 1 to 1.4 cm³ on day 62.

The rats generally appeared to exhibit normal behavior and appetite and did not appear to lose weight. The fact that the rats did not die of infections suggested that

TABLE 2

EVALUATION OF THE GROWTH OF RAT MAMARY TUMORS FOLLOWING MULTIPLE EXPOSURES TO A RAPIDLY VARYING MAGNETIC FIELD

| TUMOR TYPE | FIELD STRENGTH/ FREQUENCY Tesla/KHz | TOTAL NO. OF TUMORS* | PARTIAL OR COMPLETE RESPONSE | | Total Tumors Responding | |
|---|---|---|---|---|---|---|
| | | | Interruption of Growth | Shrinkage | No. | % |
| DMBA Primary | 5/8 | 8 | 2 | 6 | 8 | 100% |
| | 15/250 | 3 | 1 | 2 | 3 | 100% |
| Total | | 11 | 3 | 8 | 11 | 100% |
| NMU Primary | 5/8 | 10 | 1 | 9 | 10 | 100% |
| | 15/250 | 5 | 1 | 3 | 4 | 80% |
| Total | | 15 | 2 | 12 | 14 | 93% |
| NMU Trans-planted | 5/8 | 2 | 0 | 0 | 0 | 0% |
| | 15/250 | 2 | 1 | 0 | 1 | 50% |
| Total | | 4 | 1 | 0 | 1 | 25% |
| 13762E/F344 Trans-planted | 5/8 | 4 | 1 | 3 | 4 | 100% |
| | 15/250 | 2 | 1 | 1 | 2 | 100% |
| Total | | 6 | 2 | 4 | 6 | 100% |

*Includes multiple tumors of rats having primary induced tumors.

It can be seen from the above table that the method of the present invention is useful for treating a variety of malignacies, although the response varies according to the type of tumor. Accordingly, the method has general applicability to malignancy treatment.

EXAMPLE 3

Twelve rats having primary DMBA-induced mammary carcinomas were treated daily with a conventional Magneform machine. Primary mammary gland carcinoma induced by a carcinogen, such as DMBA or NMU, is highly virulent, as outlined in substantial detail in P. M. Guillino, et al., *Journal of the National Cancer Institute*, Vol. 54, no. 2, February 1974. It is common for such a tumor in a rat to increase in size by about 10-30 fold in about 30 days, and if left untreated almost invariably will ulcerate within about 45 days.

Ten of the rats are treated daily with 20 pulses at 5 Tesla and 8 KHz. Their tumor volumes on the 1st and 30th days are listed in table 3 below:

TABLE 3

| | Tumor Volume (cm³) Day 1 | Tumor Volume (cm³) Day 30 |
|---|---|---|
| 1. | 1.6 | 1.95 |
| 2. | 1.2 | 3.65 |
| 3. | 2.1 | 1.2 |
| 4. | 1.4 | 3.81 |
| 5. | 0.9 | 0.42 |
| 6. | 3.01 | 3.81 |
| 7. | 0.38 | 0.45 |
| 8. | 2.1 | 8.18 |
| 9. | 6.79 | 8.88 |
| 10. | 1.1 | 0.85 |

It can be seen from the above table that after thirty days the tumors were either diminished in size, stabilized, or at least controlled relative to untreated tumors. Furthermore, all of the rats were alive after 60 days, some with stabilized or reduced tumors, although one rat was clearly terminal at 60 days.

the immune systems functioned normally.

Although the invention has been described in terms of a preferred embodiment, modifications obvious to one with ordinary skill in the art may be made without departing from the scope of the invention. Although malignant cell inactivation is effected in the absence of more conventional selective tumor cell destruction procedures, such as irradiation therapy or chemotherapy, it is understood that the magnetic therapy practiced in accordance with the present invention may be used in conjunction with other therapeutic procedures.

Various features of the invention are set forth in the following claims:

What is claimed is:

1. A method for treating a living animal having malignant cells in its body comprising
    placing the animal or a part of the animal having malignant cells to be treated within a high intensity pulsed magnetic field treatment region,
    generating with the high intensity pulsed magnetic field treatment region a pulse of a high intensity, rapidly oscillating magnetic field having an intensity in the range of from about 1 Tesla to about 100 Tesla and a frequency in the range of from about 5 kHz to about 1000 kHz, the polarity of said magnetic field reversing during each oscillation,
    exposing said animal or part of said animal within said high intensity pulsed magnetic field treatment region to said oscillating high intensity magnetic field pulse, and
    generating sufficient additional high intensity magnetic pulses within said treatment region of like intensity, frequency and reversing polarity to expose said animal or part of said animal to the same and thereby selectively deactivate malignant cells within said animal.

2. A method according to claim 1 wherein said pulsed magnetic field has an intensity of between about 1 and about 50 Tesla.

3. A method according to claim 1 wherein the body part is exposed to between about 10 and about 1000 pulses at a single tumor abatement therapy session.

4. A method according to claim 3 where a plurality of said sessions are employed.

5. A method of selectively deactivating malignant mammalian cells relative to normal mammalian cells, the method comprising placing material having both living malignant mammalian cells and living normal mammalian cells within a high magnetic field region, and generating within said high magnetic field treatment region a plurality of pulses of a high intensity oscillating magnetic field having an intensity of between about 1 and about 100 Tesla and a frequency of between about 5 and about 100 kHz, the polarity of said high intensity magnetic field reversing in each oscillation of the respective pulse.

6. A method of selectively deactivating malignant cells in an animal with such malignant cells in its body, the method comprising providing apparatus having a high magnetic field treatment region and which produces, within said region, pulses of a decaying, oscillating high intensity magnetic field having an intensity within said region of between about 1 and about 100 Tesla and an oscillation frequency of between about 5 and about 1000 kHz, the polarity of said magnetic field reversing in each oscillation, placing an afflicted animal or body part of an afflicted animal in said region so as to be exposed to the oscillating magnetic field of said intensity and frequency when said apparatus is actuated, and actuating said apparatus a plurality of times to subject the animal or part thereof to multiple pulses of said oscillating magnetic field.

7. A method for selectively deactivating tumor cells in living biological material comprising the steps of placing living biological material containing malignant cells to be selectively deactivated, and having a resistance above 10 ohms-cm, within a high intensity magnetic field coil, discharging a charged high voltage capacitor in series circuit connection through the high intensity magnetic field coil to produce a damped, oscillating, very high intensity magnetic field pulse within the high intensity magnetic field coil containing the living biological material, said magnetic field pulse having an initial magnetic field intensity in the range of from about 1 to about 100 Tesla and an oscillation frequency in the range of from about 5 kHz to about 1000 kHz, with said magnetic field decaying in intensity and reversing in polarity with each oscillation of said pulse at said oscillation frequency, subsequently charging the high voltage capacitor and discharging the charged capacitor through the high intensity magnetic field coil such that the biological material within the high intensity magnetic field coil is subjected to a plurality of said damped, oscillating, very high intensity magnetic field pulses having an initial magnetic field intensity in the range of from about 1 to about 100 Tesla and an oscillation frequency in the range of from about 5 kHz to about 1000 kHz, and removing the living biological material from within the high intensity magnetic field coil.

8. A method in accordance with claim 7 wherein said living biological material is a living animal or part thereof.

9. A method in accordance with claim 8 wherein said animal or part thereof is subjected to a plurality of therapy sessions over an extended treatment period, with up to 1000 of said pulses of high intensity oscillating magnetic field being applied to said animal or part thereof during each therapy session.

10. A method in accordance with claim 7 wherein the electrical resistance of said living biological material is greater than 25 ohms-cm.

11. A method in accordance with claim 7 wherein said living biological material is subjected to from about 10 to about 100 of said high intensity magnetic field pulses within the high intensity magnetic field coil.

12. A method in accordance with claim 9 wherein the total exposure time of said animal or part thereof to said plurality of high intensity magnetic field pulses is from about 100 microseconds to about 1 second during each of said therapy sessions.

13. A method in accordance with claim 7 wherein said high intensity magnetic field pulses produce substantially no heating of the living biological material.

14. A method in accordance with claim 9 wherein selective deactivation of tumor cells is accomplished without substantial damage to the animal immune system.

15. A method in accordance with claim 14 wherein said animal is a human.

* * * * *